US011766338B1

(12) United States Patent
Simonson

(10) Patent No.: US 11,766,338 B1
(45) Date of Patent: Sep. 26, 2023

(54) METHOD AND APPARATUS FOR PLACEMENT OF A REDUCED VERTEBRAL BODY REPLACEMENT DEVICE DURING A SURGICAL OPERATION ON THE CERVICAL PORTION OF THE SPINE INCLUDING INTO A TRANSCORPOREAL VOID

(71) Applicant: Robert E. Simonson, Boca Raton, FL (US)

(72) Inventor: Robert E. Simonson, Boca Raton, FL (US)

( * ) Notice: Subject to any disclaimer, the term of this patent is extended or adjusted under 35 U.S.C. 154(b) by 0 days.

(21) Appl. No.: 18/106,194

(22) Filed: Feb. 6, 2023

(51) Int. Cl.
*A61F 2/44* (2006.01)
*A61F 2/46* (2006.01)

(52) U.S. Cl.
CPC .............. *A61F 2/44* (2013.01); *A61F 2/4611* (2013.01)

(58) Field of Classification Search
CPC . A61B 17/70; A61B 17/7076; A61F 2/30744; A61F 2/44; A61F 2/442; A61F 2/4425; A61F 2/446; A61F 2/4465; A61F 2002/2835; A61F 2/4611; A61F 2/4455; A61F 2220/0025; A61F 2002/30841; A61F 2/28
See application file for complete search history.

(56) References Cited

U.S. PATENT DOCUMENTS

| | | | |
|---|---|---|---|
| 4,341,206 A | 7/1982 | Perett et al. | |
| 5,015,247 A | 5/1991 | Michelson | |
| 5,180,382 A | 1/1993 | Frigg et al. | |
| 5,246,458 A | 9/1993 | Graham | |
| 5,324,290 A | 6/1994 | Zdeblick | |
| 5,364,399 A | 11/1994 | Lowery et al. | |
| 5,549,612 A | 8/1996 | Yapp | |
| 5,591,235 A | 1/1997 | Kuslich | |

(Continued)

FOREIGN PATENT DOCUMENTS

WO   WO 2010063111 A1   6/2010

OTHER PUBLICATIONS

European Spine Journal, Jan. 3, 2007, Gun Choi et al.
(Continued)

*Primary Examiner* — Seema Mathew
(74) *Attorney, Agent, or Firm* — Burr & Forman LLP; Jeffrey H. Kamenetsky

(57) ABSTRACT

A method of performing a transcorporeal procedure including placement of a Vertebral Body Replacement device into a transcorporeal void within a cervical spine is disclosed. The method includes creating a working channel through a vertebral body of a vertebra by removing at least a portion of the vertebral body of the vertebra, beginning anteriorly and extending inwardly toward the epidural space, the working channel extending from an anterior wall through a posterior wall, and placing the Vertebral Body Replacement device within the working channel, the placement of the Vertebral Body Replacement device leaving the inferior and superior endplates to perform their function and leaving at least a portion of the intervertebral disc functional thereby avoiding an intervertebral fusion to an adjacent vertebra, where the Vertebral Body Replacement device has at least one of a width of less than 12 millimeters and a diameter of less than 12 millimeters.

18 Claims, 5 Drawing Sheets

(56) References Cited

U.S. PATENT DOCUMENTS

| | | | |
|---|---|---|---|
| 6,149,686 A * | 11/2000 | Kuslich | A61F 2/4455 623/17.11 |
| 6,248,110 B1 | 6/2001 | Reiley | |
| 6,419,705 B1 | 7/2002 | Erickson | |
| 6,436,102 B1 | 8/2002 | Ralph et al. | |
| 6,517,544 B1 * | 2/2003 | Michelson | A61B 17/1659 606/85 |
| 6,679,886 B2 | 1/2004 | Weikel et al. | |
| 7,094,239 B1 | 8/2006 | Michelson | |
| 7,128,760 B2 | 10/2006 | Michelson | |
| 7,160,304 B2 | 1/2007 | Michelson | |
| 7,226,481 B2 | 6/2007 | Kuslich | |
| 7,303,565 B2 | 12/2007 | Buttermann | |
| 7,803,188 B2 | 9/2010 | Justis et al. | |
| 7,867,263 B2 | 1/2011 | Lowry | |
| 7,905,885 B2 | 3/2011 | Johnson et al. | |
| 8,163,021 B2 | 4/2012 | Lowry | |
| 8,167,948 B2 | 5/2012 | Paul et al. | |
| 8,241,363 B2 * | 8/2012 | Sommerich | A61F 2/4611 606/57 |
| 8,425,569 B2 | 4/2013 | O'Farrell | |
| 8,475,533 B1 | 7/2013 | Castro | |
| 8,879,934 B2 | 11/2014 | Kameda | |
| 8,979,934 B2 | 3/2015 | Kirshman | |
| 9,044,338 B2 | 6/2015 | Schaller | |
| 9,962,166 B1 * | 5/2018 | Sachs | A61F 2/30744 |
| 10,064,735 B1 | 9/2018 | Simonson et al. | |
| 10,137,000 B1 | 11/2018 | Simonson et al. | |
| 10,751,192 B1 | 8/2020 | Simonson et al. | |
| 11,000,290 B1 | 5/2021 | Sachs et al. | |
| 11,083,593 B1 | 8/2021 | Simonson et al. | |
| 11,523,912 B1 | 12/2022 | Simonson et al. | |
| 2001/0056302 A1 | 12/2001 | Boyer et al. | |
| 2002/0068974 A1 | 6/2002 | Kuslich | |
| 2003/0004575 A1 | 1/2003 | Erickson | |
| 2003/0065396 A1 | 4/2003 | Michelson | |
| 2003/0125747 A1 | 7/2003 | Sproul | |
| 2003/0181982 A1 | 9/2003 | Kuslich | |
| 2003/0195518 A1 | 10/2003 | Cragg | |
| 2006/0111714 A1 | 5/2006 | Foley | |
| 2009/0076555 A1 | 3/2009 | Lowry et al. | |
| 2009/0143716 A1 * | 6/2009 | Lowry | A61B 17/1757 606/86 R |
| 2009/0164018 A1 * | 6/2009 | Sommerich | A61F 2/4611 623/17.16 |
| 2009/0240334 A1 | 9/2009 | Richelsoph | |
| 2009/0248163 A1 * | 10/2009 | King | A61F 2/4611 606/86 A |
| 2010/0152793 A1 | 6/2010 | Lowry et al. | |
| 2012/0004730 A1 * | 1/2012 | Castro | A61F 2/44 623/17.16 |
| 2012/0265303 A1 * | 10/2012 | Refai | A61F 2/4465 623/17.11 |
| 2012/0310354 A1 * | 12/2012 | Ullrich, Jr. | A61F 2/4465 623/17.16 |
| 2013/0190875 A1 * | 7/2013 | Shulock | A61F 2/4601 623/17.12 |
| 2014/0156006 A1 * | 6/2014 | Bannigan | A61F 2/44 623/17.15 |
| 2014/0277458 A1 | 9/2014 | Lauryssen | |
| 2015/0148907 A1 * | 5/2015 | Kleiner | A61B 17/8816 606/94 |
| 2016/0374819 A1 | 12/2016 | Ballard | |
| 2017/0290678 A1 * | 10/2017 | Olmos | A61F 2/4657 |
| 2018/0078386 A1 * | 3/2018 | Kieser | A61F 2/30942 |
| 2019/0314162 A1 * | 10/2019 | McLaughlin | A61F 2/44 |
| 2019/0350673 A1 * | 11/2019 | Kieser | A61B 90/39 |
| 2020/0000595 A1 * | 1/2020 | Jones | A61F 2/30 |

OTHER PUBLICATIONS

Brochure—Medtronic Sofamor Danek—"ATLANTIS™ Anterior Cervical Plate System Surgical Technique" by Volker K.H. Sonntag, M.D., Barrow Neurological Institute, Regis W. Haid, Jr., M.D., Emory Clinic, Stephen M. Papadopoulos, Barrow Neurological Institute, M.D.

510(k) premarket notification of intent to market and device description of Skyline® Anterior Cervical Plate System, Uniplate® Anterior Cervical Plate System, and Uniplate® 2 Anterior Cervical Plate System, Jul. 25, 2013, Submitted by Medos International Sàrl, Switzerland, DePuy Spine, Inc., Raynham, Massachusetts and Kirsten Lehmuller, Raynham, Massachusetts.

Surgical Technique & Ordering Information, Anterior Cervical Plate System for the Skyline ACP System Description, DePuy Spine Inc., a Johnson & Johnson company, designing surgeons Curtis A. Dickman, MD, Barrow Neurological Institute, Jeffrey S. Fischgrund, MD, William Beaumont Hospital, Michael G. Fehlings, MD, Ph.D., FRCSC, University of Toronto, Michael W. Groff, MD, Indiana University, Robert F. Heary, MD, UMDNJ, New Jersey Medical School, Mark E. Shaffrey, MD, University of Virginia Health System, pp. 1-24.

Non-Final Office Action dated May 9, 2023, U.S. Appl. No. 18/104,612, United States Patent and Trademark Office.

Summary of Safety and Effectiveness FDA Approval Letter Apr. 20, 2001, pp. 1-18, Published Mar. 3, 2023 (Year: 2003).

* cited by examiner

METHOD AND APPARATUS FOR PLACEMENT OF A REDUCED VERTEBRAL BODY REPLACEMENT DEVICE DURING A SURGICAL OPERATION ON THE CERVICAL PORTION OF THE SPINE INCLUDING INTO A TRANSCORPOREAL VOID

RELATED APPLICATIONS

Not applicable

FEDERALLY SPONSORED RESEARCH OR DEVELOPMENT

Not applicable

TECHNICAL FIELD

The present disclosure relates to vertebral body replacement devices and to using a vertebral body replacement device as an implant in the cervical spine wherein the vertebral body replacement device has a width of less than twelve millimeters. The present disclosure also relates to using a vertebral body replacement device that has a width of less than twelve millimeters for the purpose of placement within a transcorporeal void created in the cervical spine during a surgical procedure.

BACKGROUND

In the spine, a motion segment includes the intervertebral disc and associated anatomy and the two adjacent vertebrae all of which allow for the movement that takes place between two vertebrae. A vertebral body replacement device eliminates the movement of a spinal motion segment and is therefore subjected to significant loads as it provides support to the subject vertebrae. It has been determined that since their inception, vertebral body replacement devices require a large, broad base sized to approximate the width of the vertebrae or a large portion of the width of the vertebra being replaced. Providing the necessary support typically requires that the width of the device is twelve millimeters or greater than twelve millimeters, and in some occasions fourteen or more millimeters.

The natural motion that occurs between vertebrae is what allows natural twisting and turning movements humans perform every day and rarely give any thought to. Located between two vertebrae is an intervertebral disc. This disc resides between the two vertebral bodies separating the bodies and allows for movement. The intervertebral disc is a critical component of what makes up a joint complex between two vertebrae. Anteriorly, the joint complex includes the disc, the anterior longitudinal ligament and the endplates along with other anatomic features. Posteriorly, it includes the facets, pedicles, lamina, neural foramen, ligaments, and more. The joint complex is actually quite complex and it is functionally eliminated when a vertebral body replacement device is used. In the past, when a vertebral body replacement device 12 mm or more was used in the cervical spine it was placed between at least two individual adjacent vertebrae, filling the space of at least one removed intervertebral disc and often filling the space of at least a removed intervertebral disc and a portion of one or more vertebrae, thus resulting in the elimination of the motion of the subject disc joint complex. Removing an intervertebral disc greatly destabilizes a spinal segment, the additional step of removing a portion of one or more vertebrae destabilizes the spine even more. It has been determined that up until this disclosure, to qualify as a vertebral body replacement device, a vertebral body replacement device must have a minimum width of twelve millimeters or ideally more than twelve millimeters to restabilize the spinal segment and handle the loads the spine receives on a regular basis.

In the field of orthopedic and neurological surgery of the spine the vocabulary is specific and specific words have very precise meaning. Additionally, regulatory agencies of the government want a precise understanding of the devices they regulate. This is accomplished by a clear understanding of precise terms and the standards of the devices they regulate.

This means the United States Food and Drug Administration (FDA) and the surgical community have very clear guidance on the design and standards of spinal devices including the implants called Vertebral Body Replacement devices. In order for an implant to be called by a particular name, the implant must meet all the requirements placed upon an implant of that name. For example, for an implant to be called a Vertebral Body Replacement (VBR) device the implant will have to undergo very precise and extensive testing, often by an independent lab, in order to meet the requirements set out by the FDA in order to qualify for the term VBR device. These requirements can include among others, biocompatibility analysis, materials analysis, fatigue criteria, shear strength, crush strength, size analysis, shape analysis, pull out resistance testing, subsidence analysis, predicate analysis, labeling analysis, indications for use analysis, contraindications analysis, sterilization analysis, bioburden analysis, and more. The purpose of this is to assure the devices do not vary much from predicate devices and that often leads to little variation in the dimensions of devices. A variation in dimensions or materials usually leads to a device being rejected or failing to withstand the relentless testing requirements and analysis portions of the qualifying process.

When a device manufacturer uses the term vertebral body replacement device, a surgeon will know the device has met all the extensive requirements to meet the definition of that term. If the device cannot pass all of the tests laid out by the FDA to qualify as a VBR device, the FDA will not allow a device to be referred to as a VBR device. The penalties for calling a device by a name not approved by the FDA are quite severe. If a device is going to be called a VBR device, the FDA must agree in advance that the device passed the testing requirements along with all the other standards laid out for a device to meet that definition. Improper labeling is not permitted.

For example, an anterior cervical plate is placed across the front of two or more vertebrae to allow for interbody fusion to occur after discectomy and repair. Anterior cervical plates are assigned a product code of KWQ and they must duly pass all the tests required of a KWQ as well as meet the specifications laid out for such a device the regulatory or medical device field use of the three letter codes is common.

A KWQ anterior cervical plate may be used in conjunction with an ODP intervertebral fusion device. An intervertebral fusion device, recognized for use in an intervertebral disc space of the cervical spine is given the product code: ODP. An ODP intervertebral fusion device, depending upon the indications for use the device has been cleared for, may be used with or without an anterior cervical plate. The idea is to be very clear as to what particular devices have been cleared for to assure that the use of devices stays within the direct function they have been analyzed and tested for.

Similarities in materials or form do not translate into different uncleared applications or indications. What might be perceived by one outside of the field of neurosurgery as similar applications may actually contain great changes in the demands and requirements placed upon a device clinically. The patient must always come first and a device must be studied in the actual application before being used in such a manner or assumed to work in such a manner.

For example, an ODP device is a cervical intervertebral fusion device for placement with bone graft between two vertebrae with intact or mostly intact endplates. This puts the ODP devices against the hard firm bone that makes up the exterior surface of a vertebral endplate. An ODP device must actually go against two endplates, the endplate of the vertebra above and the endplate of the vertebra below replacing an intervertebral disc and functioning as a spacer. The FDA defines the Technical Method of an ODP device as: "Acts as a disc spacer and holds bone graft." Target Area: "Intervertebral disc space". This means the device has been analyzed for use in that specific application. Further analysis will determine if the device can be used alone or if it must be used in conjunction with an anterior cervical plate or if it can function with or without a plate. A Vertebral Body Replacement device, recognized for use in the cervical spine is given the product code; PLR. A PLR device has the broader Target Area of: cervical spine. That means the device has been analyzed and demonstrated as safe and effective for the broader area within the cervical spine including in contact with bone marrow.

In order for an ODP device to be used in the manner in which it has been determined to function, it must be in contact with the vertebral endplates which are made up of hard cortical bone.

On the other hand a PLR VBR device is used when a partial vertebrectomy has been performed. This means a portion of at least one vertebra has been removed. This creates a different environment in which the implant must perform. The PLR VBR is placed when the hard cortical bone of a vertebra has been removed, therefore revealing the much softer interior bone called cancellous bone. This bone is sometime described as being spongy. The cellular make up of cancellous bone is very different than that of cortical endplate bone. The bone in which a PLR VBR is placed is the red bone marrow of the body. The healing environment within bone marrow is different than the bone healing environment outside of bone marrow.

These are just examples of the importance of definitions and descriptions of devices used in medicine in general and in spine surgery in specific. Assumptions are not permitted and definitions have direct and clear meanings.

SUMMARY

Disclosed herein is an inventive method of using a specific type of implant called a Vertebral Body Replacement device or VBR device in a surgical procedure upon a cervical spine wherein the VBR device has a width or a diameter after placement of less than twelve millimeters. This is in direct contrast to previous VBR devices which have widths that begin at twelve millimeters and in many cases are more than 12 millimeters.

The disclosed dimensions of a VBR device with a width or diameter of less than twelve millimeters will permit surgeons to remove less bone from the cervical vertebra of a patient when a surgeon determines that removing less bone from a patient's cervical vertebra reduces risk to the patient.

Previously, VBR devices have been used for a broad sweeping removal of vertebral bone which is usually performed after the complete removal of an intervertebral disc. Combined with removal of an intervertebral disc, removal of significant portions of a vertebra greatly destabilizes the vertebral motion segment. A VBR device with a width or diameter of less than twelve millimeters will allow for the practice of reduced disruption of healthy bone leaving the spinal segment with greater stability during a vertebral body replacement procedure.

Typically, a surgical procedure using a Vertebral Body Replacement device requires removal of a width of bone that is at least twelve millimeters in width in order to fit an implant. This has been considered a requirement in order to maintain a perceived appropriate ratio of Vertebral Body Replacement device width to vertebral body width.

A Vertebral Body Replacement device with a width or a diameter of less than twelve millimeters will also allow for the device to be used more easily, for example, in a transcorporeal surgical procedure, as discussed below. Notably, a transcorporeal surgical procedure requires an implant capable of being placed within a single vertebral body not between two different vertebral bodies. Being placed within one vertebral body requires a Vertebral Body Replacement device of reduced dimensions.

In one aspect of the present disclosure, a method of placing a Vertebral Body Replacement device between two vertebral endplates of a vertebra in a cervical spine is provided. The method includes creating a void between the two endplates of the vertebra of the cervical spine, and placing the Vertebral Body Replacement device into the void created between the two endplates, the Vertebral Body Replacement device having at least one of a width of less than 12 millimeters and a diameter of less than 12 millimeters.

In one embodiment of this aspect, the method further includes providing a series of Vertebral Body Replacement devices and selecting at least one Vertebral Body Replacement device from the series of Vertebral Body Replacement devices to place into the void between the two endplates. In another embodiment, the method further includes providing a series of Vertebral Body Replacement devices, and selecting at least one Vertebral Body Replacement device from the series of Vertebral Body Replacement devices to place into the void between the two endplates. In another embodiment, the method further includes providing a plurality of Vertebral Body Replacement devices for placement into the cervical spine, wherein at least one of the plurality of Vertebral Body Replacement devices has dimensions different from other Vertebral Body Replacement devices, selecting at least one Vertebral Body Replacement device from the plurality of Vertebral Body Replacement devices, and placing the selected at least one Vertebral Body Replacement device into the cervical spine. In another embodiment, the Vertebral Body Replacement device includes a space for placement of bone graft therein. In another embodiment, the Vertebral Body Replacement device has been given a PLR product code from the Food and Drug Administration (FDA).

In another aspect of the disclosure, a method of placing an implant into a transcorporeal void created in at least one vertebra of the cervical spine is provided. The method includes creating a void in a vertebral body of the at least one vertebra, the void beginning anteriorly and directed posteriorly creating an exit at a back of the vertebral body, and placing the implant into the void between a superior endplate and an inferior endplate of the at least one vertebra, the implant being a Vertebral Body Replacement device, the Vertebral Body Replacement device having at least one of a width of less than 12 millimeters and a diameter of less than 12 millimeters.

In one embodiment of this aspect, during and after placement of the implant, the superior endplate and the inferior endplate of the at least one vertebra remain functionally intact. In another embodiment, the Vertebral Body Replacement device has been given a PLR product code from the Food and Drug Administration (FDA). In another embodiment, the method further includes, providing a series of Vertebral Body Replacement devices, and selecting at least one Vertebral Body Replacement device from the series of Vertebral Body Replacement devices to place into the void between the superior endplate and the inferior endplates. In another embodiment, the method further includes providing a plurality of Vertebral Body Replacement devices for placement into the cervical spine, wherein at least one of the plurality of Vertebral Body Replacement devices has dimensions different from other Vertebral Body Replacement devices, selecting at least one Vertebral Body Replacement device from the plurality of Vertebral Body Replacement devices, and placing the selected at least one Vertebral Body Replacement device into the cervical spine. In another embodiment, the Vertebral Body Replacement device includes a space for placement of bone graft therein.

In another aspect of the disclosure, a method of performing a transcorporeal procedure including placement of a Vertebral Body Replacement device into a transcorporeal void within a cervical spine is provided. The method includes creating a working channel through a vertebral body of a vertebra by removing at least a portion of the vertebral body of the vertebra, beginning anteriorly and extending inwardly toward the epidural space, the working channel extending from an anterior wall through a posterior wall, and placing the Vertebral Body Replacement device within the working channel, the placement of the vertebral body replacement device leaving a superior endplate and an inferior endplate to perform their function and leaving at least a portion of the intervertebral disc functional thereby avoiding an intervertebral fusion to an adjacent vertebra, the Vertebral Body Replacement device having at least one of a width of less than 12 millimeters and a diameter of less than 12 millimeters.

In one embodiment of this aspect, the method further includes providing a series of Vertebral Body Replacement devices, and selecting at least one Vertebral Body Replacement device from the series of Vertebral Body Replacement devices to place into the void between the superior endplate and the inferior endplate. In another embodiment, the method further includes providing a plurality of Vertebral Body Replacement devices for placement into the cervical spine, wherein at least one of the plurality of Vertebral Body Replacement devices has dimensions different from other Vertebral Body Replacement devices, selecting at least one Vertebral Body Replacement device from the plurality of Vertebral Body Replacement devices, and placing the selected at least one Vertebral Body Replacement device into the cervical spine.

In another embodiment, the Vertebral Body Replacement device includes a space for placement of bone graft therein. In another embodiment, the width of the Vertebral Body Replacement device is less than twelve millimeters and the height of the Vertebral Body Replacement device is equal to the width. In another embodiment, the Vertebral Body Replacement device has been given a PLR product code from the Food and Drug Administration (FDA).

In another aspect of the disclosure, a method of providing a Vertebral Body Replacement device for placement into a cervical spine during the course of an anterior spinal surgical procedure upon the cervical spine wherein the Vertebral Body Replacement device has a width of less than twelve millimeters is provided. In one embodiment of this aspect, the method further includes providing a series of Vertebral Body Replacement devices, and selecting at least one Vertebral Body Replacement device from the series of Vertebral Body Replacement devices for placement into the cervical spine. In one embodiment of this aspect, the Vertebral Body Replacement device engages at least a portion of two adjacent vertebrae in the cervical spine. In another embodiment, the Vertebral Body Replacement device includes a space for placement of bone graft therein.

DETAILED DESCRIPTION OF THE INVENTION

Figure 1:
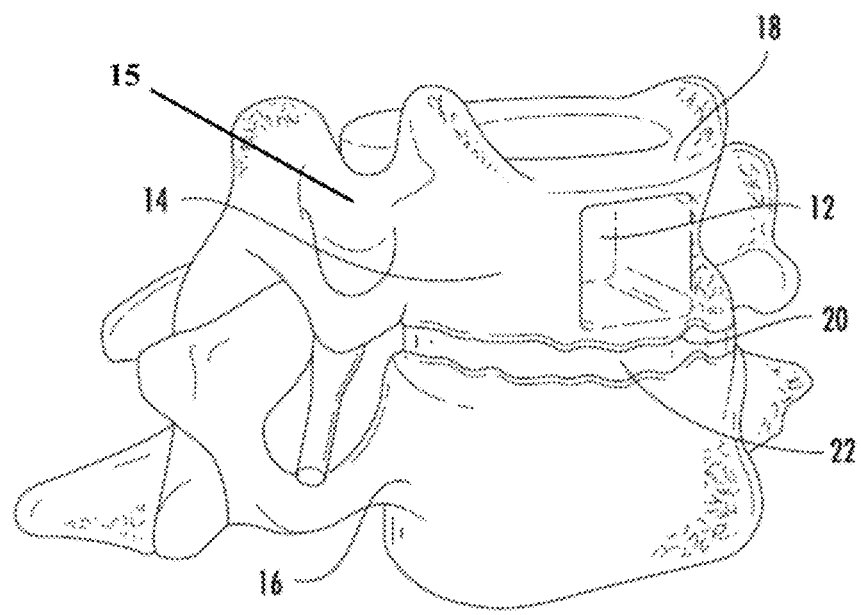
FIG. 1 illustrates a void created within a single vertebra for acceptance of a VBR implant having a width of less than 12 millimeters therein.

As discussed above, a procedure described as a transcorporeal procedure in the cervical spine, also known as an intravertebral corpectomy, has a specific definition. While the definition does not change, some people use the additional terms: single-level partial vertebral body replacement, and/or, partial replacement of a vertebral body, and/or, partial vertebrectomy. By any name, this is a procedure wherein a portion of a vertebra, referred to herein as a portion of the vertebral corpus or vertebral body, is removed and/or drilled through. In order to be referred to as an intravertebral corpectomy or a transcorporeal procedure, or any one of the other terms mentioned above, the process of removing a portion of the vertebral body begins anteriorly or anterolaterally upon the front half on a vertebral body and proceeds posteriorly or posterolaterally through the back half of the vertebral body creating an exit opening through the back wall of the vertebral body, thus creating a working channel to provide surgical access to the area behind the vertebral body.

In the present disclosure, the terms "anterior" and "posterior" with regard to the anatomy of a vertebral body in the cervical spine, can be used to refer to the anterior half of the vertebral body or the posterior half of the vertebral body. The working channel includes an entry point on the anterior half of the vertebral body and an exit point on the posterior half of the vertebral body creating a functional pathway through the vertebral body passing from the front of the vertebral body through the back of the vertebral body. The purpose of the transcorporeal procedure is to provide surgical access to the pathology that lies upon, in proximity to, or behind the vertebral body portion of a vertebra. Using the transcorporeal approach to gain access to the area behind the vertebral body, the surgeon creates a working channel. The area behind the vertebral body is sometimes referred to as the greater epidural space. This working channel represents a functional pathway from the front of the vertebra, through the vertebral body, which includes passing through a back wall of the vertebral body in order to gain functional surgical access to pathologies that lie behind the vertebral body or in the greater epidural space.

After the performance of a transcorporeal procedure, including the treatment of the pathology that the surgeon treated behind the vertebral body, the transcorporeal void which is the working channel, must either be left void or repaired with an implantable device. In one embodiment, this disclosure provides a method of repairing the void created in the process of performing the transcorporeal procedure by placing a Vertebral Body Replacement device into the void made during the creation of the working channel. The Vertebral Body Replacement device of this disclosure is also useful in other vertebral body replacement procedures as the device can be used to preserve motion with placement into a vertebral body of a single vertebra or, in another embodiment, it can be used to eliminate motion by placing the device between two vertebrae into the space of a completely or partially removed intervertebral disc. In either embodiment, the Vertebral Body Replacement device is less than 12 millimeters in width or diameter. Therefore, the implant of this disclosure can preserve motion by placement into a transcorporeal void or eliminate motion by placement between two vertebrae in the cervical spine.

For the purposes of this disclosure, the term "cervical spine" will follow the usual guidance of the FDA, which when referring to vertebral body replacement devices, the term cervical includes the second cervical vertebra (C2) through the first vertebra of the Thoracic spine (T1). This is commonly expressed as (C2-T1) which means the second through the seventh cervical vertebrae and the first and most superior of the thoracic vertebrae. In the present disclosure, unless otherwise specified, the term "device" is used interchangeably with the term "implant."

The FDA defines a Vertebral Body Replacement device as:
Device—Spinal Vertebral Body Replacement device—Cervical
Regulatory Description—Spinal intervertebral body fixation orthosis
Definition—Vertebral body replacement in the cervical spine
Physical State—Metallic or polymeric device (usually rectangular or cylindrical), with open central and lateral canals for bone graft containment, providing rigidity and structural support.
Technical Method—Provides structural support for the indicated population
Target Area—Cervical spine
Product Code— PLR As described herein, in order for a device to be given clearance to be used as a Vertebral Body Replacement device in the cervical spine, and receive the product code PLR from the FDA the device has to be submitted to rigorous testing. To date, there is not a PLR predicate that has either a width or diameter of less than twelve millimeters and this is for fairly direct reasons.

Prior to this disclosure, choosing VBR implant width has been based on trying to provide a large width to re-establish stability after performing a method of destabilizing broad bone removal when performing a partial or complete vertebrectomy in the cervical spine. Disclosed here is a method of, in one embodiment, performing a minimal partial vertebrectomy that leaves the spine stable enough to be repaired with a Vertebral Body Replacement device with a width or diameter of less than twelve millimeters. In another embodiment, the Vertebral Body Replacement device is used to engage adjacent vertebrae. In either embodiment, disclosed herein are Vertebral Body Replacement devices with a width of less than 12 millimeters, and/or a diameter of less than 12 millimeters to be used in such procedures. The Vertebral Body Replacement device and method of its use disclosed herein will allow a surgeon to remove the only the necessary amount of bone required to be removed and no more. The Vertebral Body Replacement device and method of its use of this disclosure may be used in a more stable spine or within a vertebra itself as in a transcorporeal procedure.

Also disclosed herein is a cylindrical Vertebral Body Replacement device wherein after placement, i.e., after it is placed across the vertebral body or bodies, the forward, anteriorly facing, dimension of the device is less than twelve millimeters in diameter.

In the present disclosure, the terms "void" or "defect" with regard to surgery to a cervical spine, can be used to refer to the surgically created space left by the removal of bone, intervertebral disc, and/or other tissues from the cervical spine.

Vertebral body replacement surgical methods and therefore Vertebral Body Replacement devices are naturally associated with broad sweeping decompressions, i.e., significant bone removal. It is therefore natural and intuitive to look to devices with designs that are intended to cover a large percentage of the width (measurement from side-to-side after placement) of the vertebrae they support. This is for good reason; a wider implant will provide greater support to the adjacent vertebrae and the devices will hold more bone graft and be in greater surface area contact with the bone of the vertebrae. This support is important because the removal of an intervertebral disc and removal of one or more vertebral bodies leaves the spine unstable. In order for the spine segment to heal, the spinal segment must be restabilized.

VBR devices are made to provide a wide base of support to support the vertebrae and handle heavy loads, making the use of a VBR device of less than twelve millimeters in width or diameter counterintuitive.

This disclosure provides for a method of less bone removal than has been previously anticipated leaving the vertebra in a more stable condition and therefore making a smaller implant possible. Yet in order to qualify as a PLR Vertebral Body Replacement device, the smaller device will have to pass the testing requirements created to test much larger devices designed for heavy loads. These comprehensive testing requirements further make it intuitively unnatural to look to engineering smaller VBR devices that have to pass the testing demands of much larger devices with greater material mass.

In one embodiment, the VBR device disclosed herein may be of a cylindrical form with a diameter of less than twelve millimeters. In one embodiment, the VBR device in cylindrical form as disclosed herein may be measured in diameter when the measurement of the implant diameter is taken from the forward-facing aspect of the device. The forward-facing aspect of the VBR device means the measurement is taken from the anterior or front-facing aspect of the implant as the implant will sit after placement. In this embodiment, the diameter is less than twelve millimeters.

Disclosed herein is a method of placing a device that meets the requirements of a VBR device where the device is placed either within a single vertebrae within a transcorporeal void of the cervical spine or across two adjacent vertebra, wherein after placement, the implant has a measurement of width that is less than twelve millimeters.

Further disclosed is a Vertebral Body Replacement device wherein the width of the device is less than twelve millimeters and the height of the Vertebral Body Replacement device is equal to the width of the device.

FIG. 1 illustrates a void created within a single vertebra for acceptance of a VBR device having a width of less than 12 millimeters therein.

Figure 2A:
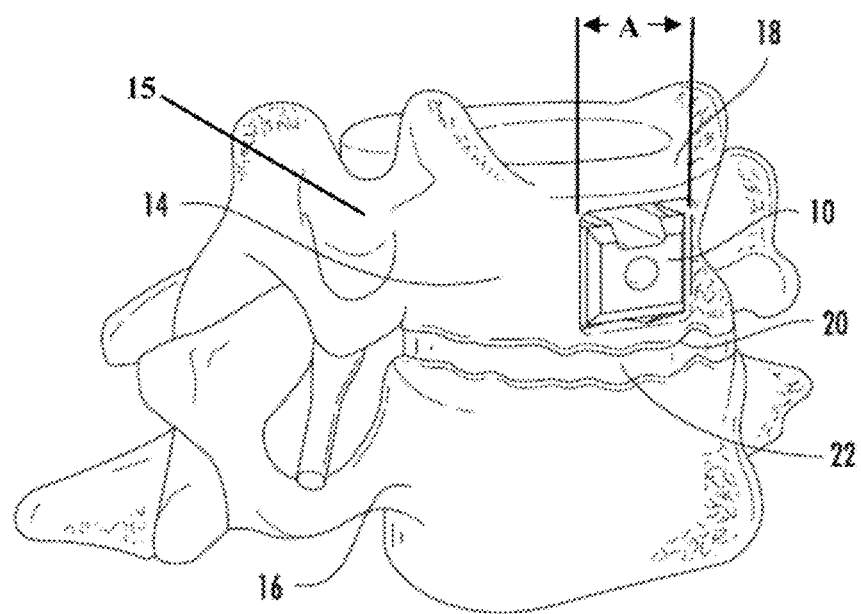
FIGS. 2A-2C illustrate the single vertebra after the insertion of the VBR implant having a width of less than 12 millimeters between two endplates.
Figure 2B:
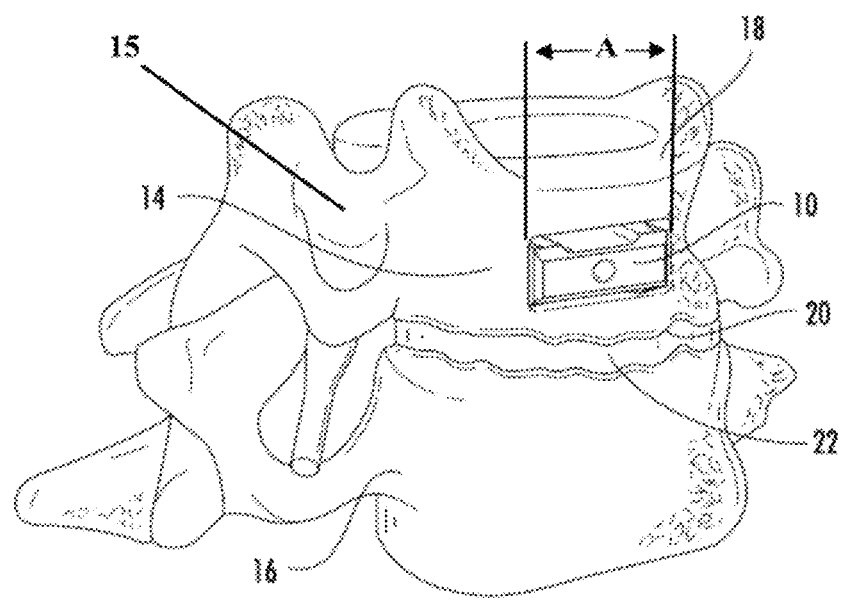
Figure 2C:
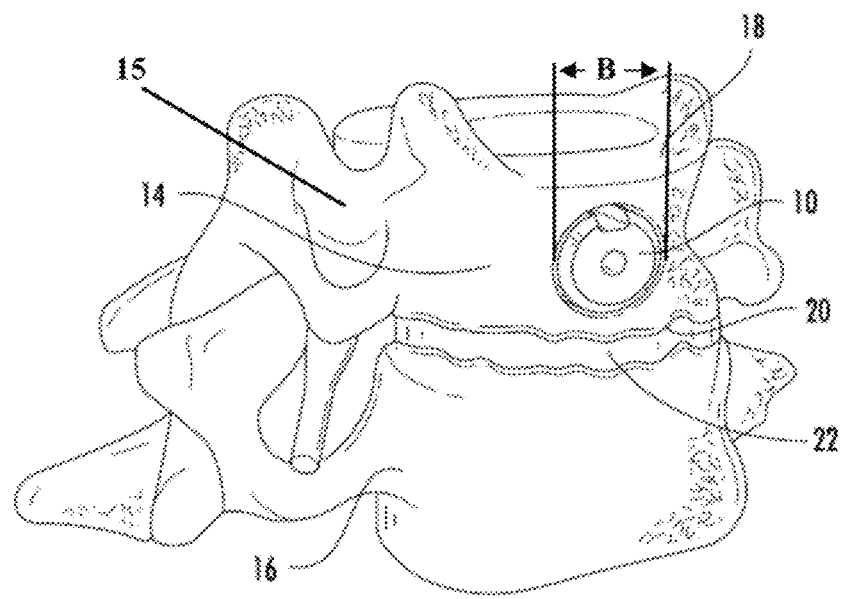

FIGS. 2A-2C illustrate the single vertebra after the insertion of a VBR device between two endplates, the VBR device having a width of less than 12 millimeters.

Figure 3A:
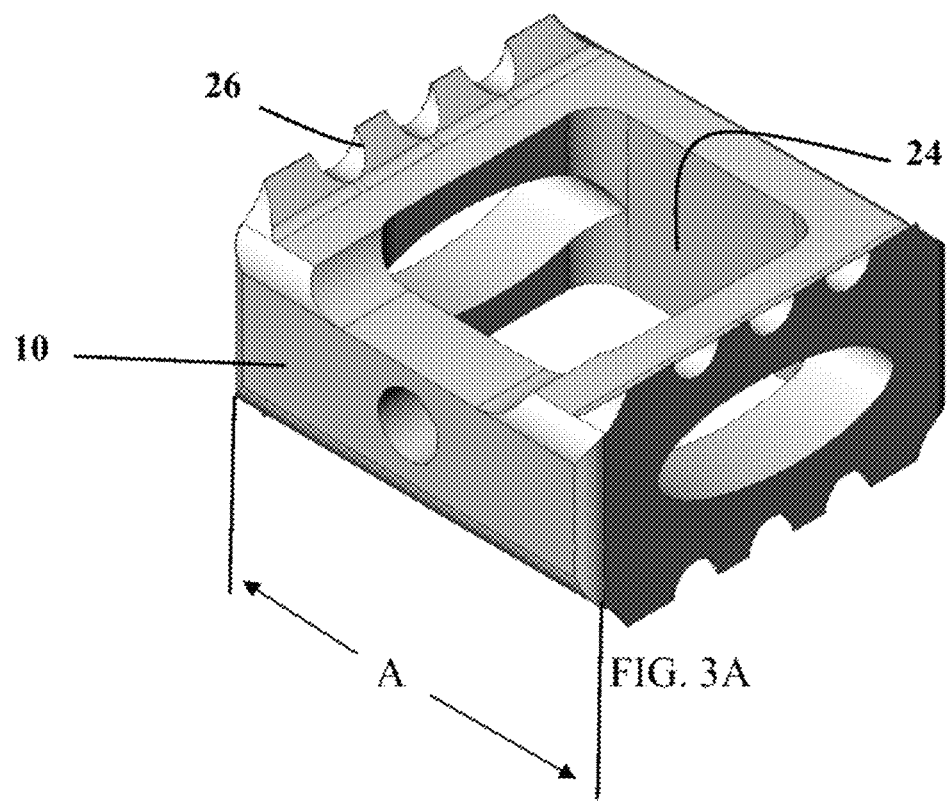
FIGS. 3A-3C illustrate alternate versions of the VBR implant having a width of less than 12 millimeters.
Figure 3B:
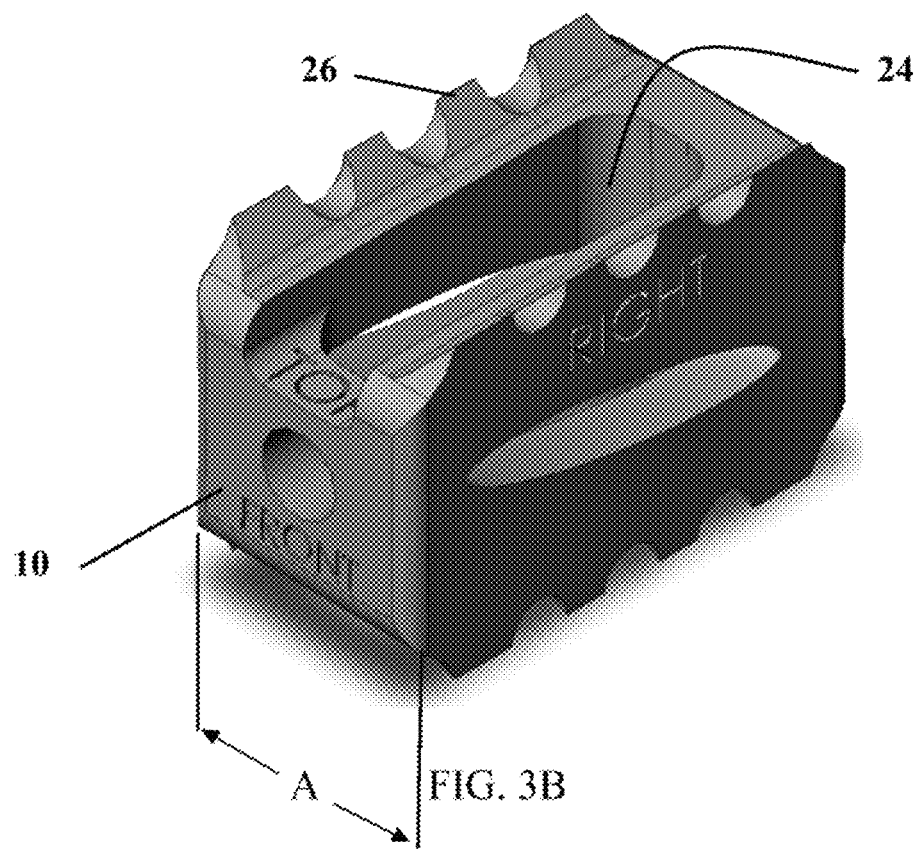
Figure 3C:
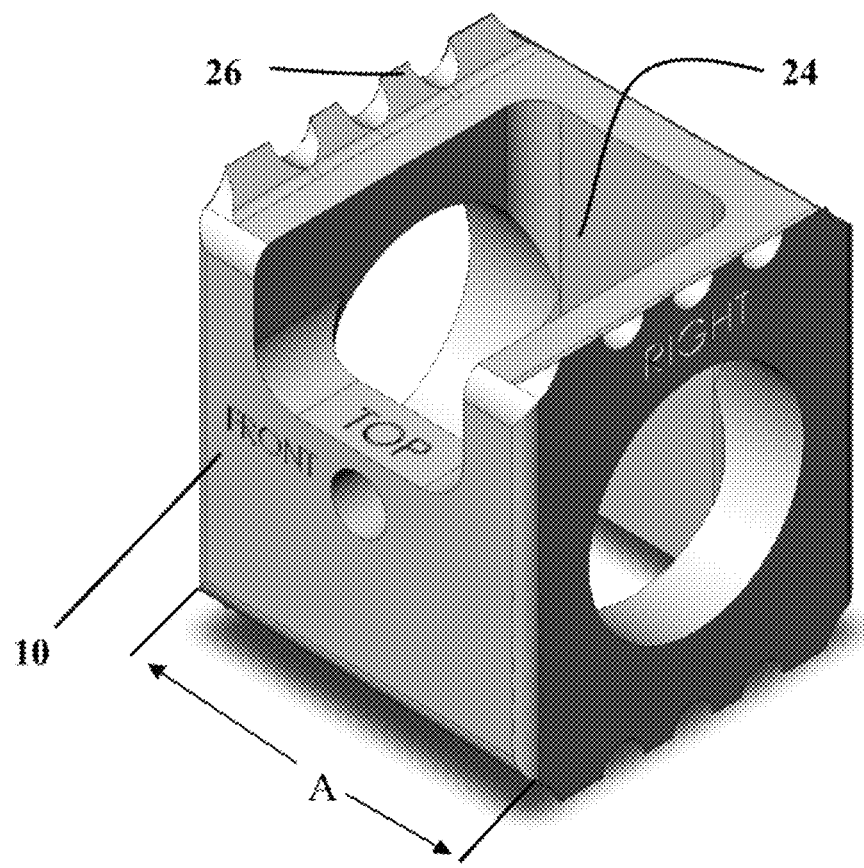

FIGS. 3A-3C illustrate alternate versions of a VBR device having a width of less than 12 millimeters.

Figure 4:
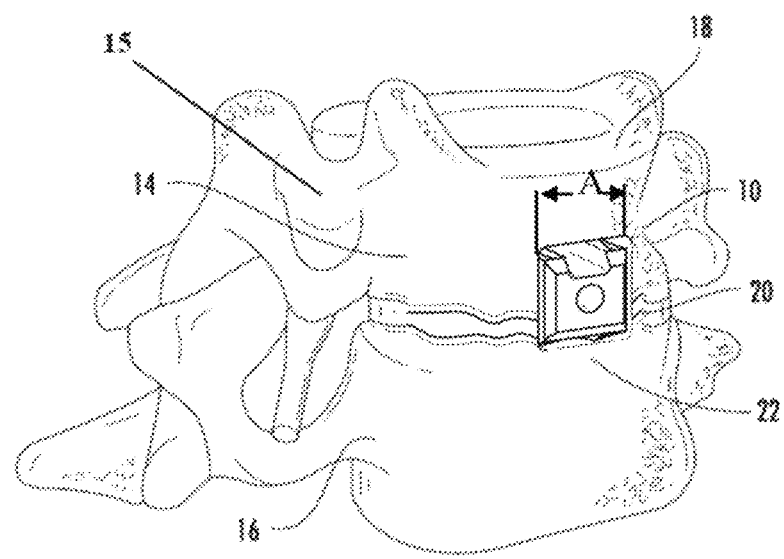
FIG. 4 illustrates a VBR implant having a width less than 12 mm engaged with at least a portion of two adjacent vertebrae.

FIG. 4 illustrates a VBR device having a width of less than 12 millimeters engaging at least a portion of adjacent vertebrae.

The figures show the method of placing of a Vertebral Body Replacement device into a void created in the vertebral body within either a single vertebra of the cervical spine or across two adjacent vertebrae of the cervical spine, where in either embodiment, the Vertebral Body Replacement device is less than 12 mm in width. The actual features of the Vertebral Body Replacement device will vary based upon anatomical needs and requirements of surgeons, patients, and regulatory bodies. However, within the requirements of surgeons, patients, and regulatory bodies, the Vertebral Body Replacement device of the present disclosure will have a width of less than 12 millimeters, or a diameter of less than 12 millimeters. Throughout this disclosure, when referring to the dimensions of the Vertebral Body Replacement device of the present disclosure, the width of the Vertebral Body Replacement device shall be less than 12 mm and/or the diameter of the Vertebral Body Replacement device shall be less than 12 mm. Therefore, even if the text of this disclosure refers to just the width being less than 12 mm, this may also include embodiments where the diameter of the Vertebral Body Replacement device is also less than 12 mm, where for instance the Vertebral Body Replacement device is spherical or includes curvature.

Referring to FIGS. 1 and 2A-2C, disclosed herein is, in one embodiment, a method of performing a transcorporeal procedure including placement of a Vertebral Body Replacement ("VBR") device 10 having a width of less than 12 mm (as shown by "A" in FIGS. 1, 2A and 2B), or a diameter less than 12 mm (as shown by "B" in FIG. 2C), into a transcorporeal void 12 within a cervical spine (not shown), the method includes creating a working channel through a vertebral body 14 of a vertebra 15, beginning anteriorly and extending inwardly toward the epidural space. Herein, the "corpus portion of the vertebra 15" may also be referred to as the vertebral body 14. A working channel through which surgery can be performed is formed when the transcorporeal void 12 is completed. The working channel extends from an anterior wall through a posterior wall. The Vertebral Body Replacement device 10 is placed within the working channel, the placement of the Vertebral Body Replacement device 10 leaving the superior endplate 18 and inferior endplate 20 to perform their function and leaving at least a portion of the intervertebral disc 22 functional thereby avoiding an intervertebral fusion to an adjacent vertebra 16.

In the present disclosure, the terms "void" or "defect," with regard to transcorporeal surgery, can be used to refer to the surgically created space within or through a vertebral body 14. It is possible that a surgeon will perform a transcorporeal procedure upon more than one vertebra 15, but in such a case, each vertebra 15 would receive a VBR device 10 to repair the surgically created transcorporeal void 12.

In one embodiment, a method of placing an implant into a surgically created void in the spine is disclosed, the method including creating a void 12 in a vertebral body 14 of a cervical vertebra 15, the void 12 beginning anteriorly and directed posteriorly, creating an exit at the back of the vertebral body 14, and placing the implant into the void 12 between a superior endplate 18 and an inferior endplate 20 of the vertebra 15, the implant being a Vertebral Body Replacement device 10 having a width of less than 12 mm.

In another embodiment, a method of placing an implant into a surgically created void 12 in the spine is disclosed, the method including creating a void 12 in a vertebral body 14 of a cervical vertebra 15, the void 12 beginning anteriorly and directed posteriorly creating an exit at the back of the vertebral body 14, and placing the implant into the void 12 below the superior endplate 18 and above the inferior endplate 20 of the vertebra 15, the implant being a Vertebral Body Replacement device 10 having a width of less than 12 mm.

The afore-mentioned greater epidural space includes the spinal canal and its contents, the neural foramen, and all the ligamentous and neural tissues such as the spinal cord, nerve roots, and intervertebral discs, among other tissues. The goal of the transcorporeal procedure is to surgically treat a spinal problem that is causing the patient to suffer and at the same time preserve the motion segment. In the spine, a motion segment, which includes an intervertebral disc 22 allows the movement that takes place between two adjacent vertebrae, i.e., 15 and 16. The disc 22 sits between the two adjacent vertebrae 15 and 16, separating the bodies and allowing for movement.

The goal of the transcorporeal procedure is to address the pathology by going through the vertebral body 14, between the superior endplate 18 and inferior endplate 20 of a single vertebral body 14 without eliminating the movement of the vertebra 15 by preserving the intervertebral disc 22 and the movement in allows. If a surgeon does not want to try to preserve the motion of the two vertebrae 15 and 16, the surgeon will not perform a transcorporeal procedure; the surgeon can simply remove the disc 22 that separates the two vertebrae 15 and 16 and access the pathology by going between the two vertebrae 15 and 16 through the now open space where the disc 22 was removed. In this case, the surgeon would now fuse the two vertebrae 15 and 16 together by using an implant, often a Vertebral Body Replacement device 10, placed between the endplates of two vertebrae 15 and 16 thus eliminating the motion segment.

While the transcorporeal procedure has been thoroughly documented to be successful and beneficial to the patient, the procedure has failed to get widespread acceptance. One of the reasons for this lack of acceptance is due to a lack of implants available to repair the working channel or void created in the process of gaining access to the greater epidural space by working through a vertebral body.

Disclosed herein is an inventive method of using a specific class of implant called a Vertebral Body Replacement (or "VBR") device 10 as the implant to be placed into a transcorporeal void 12, which is also referred to herein, when completed, as a working channel. The VBR devices 10 are from a category of implants that are associated with intervertebral use. The width of each VBR device 10 is less than 12 mm. The use of such an implant for intervertebral use would intuitively be considered to be the opposite of the use of the implant for transcorporeal use. Intervertebral use means the devices are placed between at least two vertebrae 15 and 16. VBR devices 10 are implants that are typically associated with the fusion of two or more vertebrae 15 and 16 after removing an intervertebral disc 22 and some of the bone of at least one or more vertebrae 15 and 16. What is common among VBR devices 10 is that this group of implants is typically associated with a fusion procedure which eliminates the motion between at least two vertebrae 15 and 16.

This is the opposite of the goal of performing a transcorporeal procedure. As stated earlier, the intent of a transcorporeal procedure is to avoid performing an intervertebral fusion so it is counterintuitive to look to the VBR intervertebral fusion device to perform a motion-preserving surgical procedure.

Disclosed herein is an inventive method of using a specific type of implant, a VBR device 10 that has not, heretofore, been used in conjunction with transcorporeal surgery or for use within a single vertebra 15. In accordance with the methods disclosed herein, the implant 10 may be placed for the filling, the repair, and or the support and healing of the transcorporeal void 12, i.e. working channel. This specific use of VBR device 10, placed within a transcorporeal void 12 within a single vertebra 15, has not been done before because the use of such a VBR implant 10 is counterintuitive as explained herein. The VBR device 10 has a width of less than 12 mm.

VBR devices, including the VBR device 10 having a width and/or diameter of less than 12 mm. disclosed herein, may include "teeth" 26 (shown in FIGS. 3A-3C) or significant features of engagement to keep them from sliding or moving forward or backward. This compressive force allows the teeth of the implant 10 to press into the vertebra 15 above and the vertebra 16 below the implant 10 to provide engagement. During surgery, the surgeon distracts or holds the vertebrae 15 and 16 apart from one another. Distracting or holding the vertebrae 15 and 16 apart accomplishes two primary functions. The first is it enlarges the space between the vertebrae 15 and 16 providing greater access to the greater epidural space. Secondly, the enlarged space also importantly allows for the placement of the VBR device 10. A VBR device 10 is engineered not to slide or otherwise move within bone.

During the traditional use of a VBR device 10, once the device 10 is placed into the open space between two vertebrae 15 and 16, the surgeon will release the distraction and allow the two or more vertebrae to compress down on the VBR device 10 creating engagement with the teeth pressing into the bone. This compression only increases as the patient stands up post operatively and gravity and the weight of the patient further compress the implant 10 between the vertebrae 15 and 16. This compression creates engagement that holds the implant 10 in place and facilitates healing through bone growth. The teeth also prevent the implant 10 from being easily slid into a fixed, non-distracted void such as a transcorporeal void 12 that cannot be distracted apart. As a transcorporeal void 12 is created in a single vertebra 15, i.e., a single bone, the space cannot be distracted apart to make room for the VBR device 10 having a significant number (or size) of teeth to be slid into position when implanted. The size and design of the teeth, which provide features engineered to grasp and hold position to bone and not slide, have to be taken into consideration for use in a transcorporeal application. As described, a transcorporeal procedure requires the placement of the VBR device 10 within a void 12 made in the body of a single vertebra 15.

This disclosure of the method of placing a VBR device 10 having a width and/or diameter of less than 12 mm into a transcorporeal void 12 is as mentioned counterintuitive for a number of reasons. One reason is the relationship between the implant 10 and the stability of the spinal segment. Currently, VBR devices 10 have been placed into unstable spinal segments of the cervical spine where a discectomy and partial or complete vertebrectomies have been performed. In these cases, the VBR device 10 is placed into an unstable spinal segment. The disclosed inventive method provides for a VBR device 10 to be placed into the transcorporeal void 12 in the vertebral body 14 portion of an individual vertebra 15 of the cervical spine. In such a case, the VBR device 10 performs in a spinal segment that does not have a lack of stability; the VBR device 10 must perform in a stable environment.

Further, using the VBR device 10 of the dimensions described herein in the manner described herein is counterintuitive because VBR devices 10 are designed to take advantage of a characteristic of bone and bone growth referred to as Wolff's Law. Wolff's Law teaches that bone density changes in response to changes in the functional forces on the bone. In other words, Wolff's Law teaches that bone grows when stress or pressure in applied to it. For example, this is the reason why regular exercise is vital to maintaining bone mass and strength throughout life and it is also for example, a challenge to astronauts who spend significant time in low gravity environments. Without loads, bone begins to weaken, while with loads bone begins to strengthen and grow. This is one of several reasons why the placement of a VBR device 10 into the vertebral body 14 of a single vertebra 15 has not been attempted. Traditional analysis teaches that a VBR device 10 placed into a transcorporeal void 12 will not have an adjacent vertebra 16 to press into in order to be fully and formally loaded to function as intended.

VBR devices 10 are designed to carry and function and heal growing bone under a load and this load is an important part of the healing process as it stimulates new bone growth. This intervertebral load is not available to a VBR device 10 placed into a transcorporeal void 12. Therefore bone growth has to be achieved via other assisting mechanisms. Placement of a VBR device 10 into a single vertebra 15 instead of between two vertebrae 15 and 16 under load is, with initial analysis, in contrast to Wolff's Law of bone growth and other principles that relate to bone growth and Vertebral Body Replacement devices 10.

In one embodiment, the implant of the present disclosure is a VBR device 10 having a width and/or diameter of less than 12 mm that is placed between the internal aspects of the endplates of a single vertebra 15, i.e., into the body or created defect in a vertebra 15, below the superior endplate 18 and above the inferior endplate 20 of one vertebra 15. This is different than intervertebral surgeries. Phrased differently, the method of the present disclosure includes placing a VBR device 10 into the vertebral body 14 of one vertebra 15 to fill a transcorporeal defect or hole. By contrast, prior to this disclosure, a VBR device 10 of greater than 12 millimeters was placed only between two vertebrae 15 and 16 replacing a removed intervertebral disc 22. When an intervertebral disc 22 is removed and replaced by an implant for fusion, the vertebral endplates in contact with the implant are no longer functionally intact. This means the endplates are no longer interfacing with an intervertebral disc 22 but are interfacing with a fusion implant. Thus, bone is growing into the fusion implant eliminating the motion and the traditionally healthy function of a vertebral endplate.

In one embodiment, disclosed herein is the method comprising creating a void 12 in a vertebral body 14 of a cervical vertebra 15, the void beginning anteriorly and directed posteriorly, creating an exit at a posterior aspect of the vertebral body 14 and placing an implant into the void 12 between a superior endplate 18 and an inferior endplate 20 of the vertebra 15, the implant being a Vertebral Body Replacement device 10 of less than 12 mm in width and/or diameter, leaving both endplates functionally intact.

The method of placing a VBR device 10 into a transcorporeal void 12 will necessarily require the VBR device 10 to function and promote bone growth and healing without the benefit of intervertebral compression.

In one embodiment, disclosed herein is a method of repairing and helping heal a transcorporeal void 12 by inserting within the void 12 a VBR device 10 having a width and/or diameter of less than 12 mm. An exemplary method is placing an implant into a transcorporeal void 12 created in at least one vertebra 15 of the cervical spine, the method including creating a void 12 in a vertebral body 14 of a vertebra 15, the void 12 beginning anteriorly and directed posteriorly creating an exit at the back of the vertebral body 14; and placing the implant into the void 12 between a superior endplate 18 and an inferior endplate 20 of the vertebra 15, the implant being a Vertebral Body Replacement device 10 having a width and/or diameter of less than 12 mm. The aforementioned methods described herein will allow the superior endplate 18 and the inferior endplate 20 of the vertebra 15 to remain functionally intact.

FIGS. 3A-3C illustrate alternate versions of the VBR implant 10 of the present disclosure. In each figure, space 24 is shown. Space 24 is configured to receive bone graft therein. Further, each figure illustrates a series of teeth 26 on both the top and bottom of implant 10. It should be noted that the placement, size, number, and dimension of teeth 26 shown in the figures is exemplary only, and the present disclosure is not limited to the placement, size, number, and dimension of teeth 26 shown in these figures. Each implant 10 has a width and/or diameter of less than 12 mm as shown by dimension A.

As shown in the figures, one of a plurality of VBR devices 10 can be selected for placement into the cervical spine. In one or more embodiments, at least one of the plurality of VBR devices 10 has dimensions different from other VBR devices 10. The shape, size and dimensions of the VBR devices 10 shown in the figures are not meant to be limiting in any way. The method disclosed herein can use VBR devices 10 of shapes, sizes, and dimensions not necessarily depicted in the drawing figures. In each case however, the VBR device 10 has a width and/or diameter of less than 12 millimeters. The VBR devices 10 disclosed herein contain embodiments for placement into a single vertebral body within the cervical spine or between two vertebrae within the cervical spine.

In one embodiment of the present disclosure, shown in FIG. 4, a method of providing a VBR device 10 for placement into a cervical spine during the course of an anterior spinal surgical procedure upon the cervical spine is shown. The VBR device 10 has a width of less than twelve millimeters, as shown by dimension A. As shown in FIG. 4, VBR device 10 engages at least a portion of two adjacent vertebrae 15 and 16 of the cervical spine.

The invention claimed is:

1. A method of placing a Vertebral Body Replacement device between two vertebral endplates of a single vertebra in a cervical spine, the method comprising:

creating a void between the two endplates of the vertebra of the cervical spine; and placing the Vertebral Body Replacement device into the void created between the two endplates of the single vertebra, the Vertebral Body Replacement device having at least one of a width of less than 12 millimeters and a diameter of less than 12 millimeters, the width and the diameter representing side-to-side dimensions of the Vertebral Body Replacement device after it has been placed into the void, wherein the Vertebral Body Replacement device has been given a PLR product code from the Food and Drug Administration (FDA).

2. The method of claim 1, further comprising:

providing a series of Vertebral Body Replacement devices; and selecting at least one Vertebral Body Replacement device from the series of Vertebral Body Replacement devices to place into the void between the two endplates.

3. The method of claim 1, further comprising:

providing a plurality of Vertebral Body Replacement devices for placement into the cervical spine, wherein at least one of the plurality of Vertebral Body Replacement devices has dimensions different from other Vertebral Body Replacement devices;

selecting at least one Vertebral Body Replacement device from the plurality of Vertebral Body Replacement devices; and placing the selected at least one Vertebral Body Replacement device into the cervical spine.

4. The method of claim 1, wherein the Vertebral Body Replacement device includes a space for placement of bone graft therein.

5. A method of placing an implant into a transcorporeal void created in at least one single vertebra of the cervical spine, the method comprising:

creating a void in a vertebral body of the at least one vertebra, the void beginning anteriorly and directed posteriorly creating an exit at a back of the vertebral body; and placing the implant into the void between a superior endplate and an inferior endplate of the at least one single vertebra, the implant being a Vertebral Body Replacement device, the Vertebral Body Replacement device having at least one of a width of less than 12 millimeters and a diameter of less than 12 millimeters, the width and the diameter representing side-to-side dimensions of the Vertebral Body Replacement device after it has been placed into the void, wherein the Vertebral Body Replacement device has been given a PLR product code from the Food and Drug Administration (FDA).

6. The method of claim 5, wherein during and after placement of the implant, the superior endplate and the inferior endplate of the at least one vertebra remain functionally intact.

7. The method of claim 5, further comprising:

providing a series of Vertebral Body Replacement devices; and selecting at least one Vertebral Body Replacement device from the series of Vertebral Body Replacement devices to place into the void between the superior endplate and the inferior endplate.

8. The method of claim 5, further comprising:

providing a plurality of Vertebral Body Replacement devices for placement into the cervical spine, wherein at least one of the plurality of Vertebral Body Replacement devices has dimensions different from other Vertebral Body Replacement devices;

selecting at least one Vertebral Body Replacement device from the plurality of Vertebral Body Replacement devices; and placing the selected at least one Vertebral Body Replacement device into the cervical spine.

9. The method of claim 5, wherein the Vertebral Body Replacement device includes a space for placement of bone graft therein.

10. A method of performing a transcorporeal procedure including placement of a Vertebral Body Replacement device into a transcorporeal void within a cervical spine, the method comprising:

creating a working channel through a vertebral body of a vertebra by removing at least a portion of the vertebral body of the single vertebra, beginning anteriorly and extending inwardly toward the epidural space, the working channel extending from an anterior wall through a posterior wall; and placing the Vertebral Body Replacement device within the working channel, the placement of the vertebral body replacement device leaving a superior endplate and an inferior endplate of the single vertebra to perform their function and leaving at least a portion of the intervertebral disc functional thereby avoiding an intervertebral fusion to an adjacent vertebra, the Vertebral Body Replacement device having at least one of a width of less than 12 millimeters and a diameter of less than 12 millimeters, the width and the diameter representing side-to-side dimensions of the Vertebral Body Replacement device after it has been placed into the working channel, wherein the Vertebral Body Replacement device has been given a PLR product code from the Food and Drug Administration (FDA).

11. The method of claim 10, further comprising:

providing a series of Vertebral Body Replacement devices; and selecting at least one Vertebral Body Replacement device from the series of Vertebral Body Replacement devices to place into the void between the superior endplate and the inferior endplate.

12. The method of claim 10, further comprising:

providing a plurality of Vertebral Body Replacement devices for placement into the cervical spine, wherein at least one of the plurality of Vertebral Body Replacement devices has dimensions different from other Vertebral Body Replacement devices;

selecting at least one Vertebral Body Replacement device from the plurality of Vertebral Body Replacement devices; and placing the selected at least one Vertebral Body Replacement device into the cervical spine.

13. The method of claim 10, wherein the Vertebral Body Replacement device includes a space for placement of bone graft therein.

14. The method of claim 10, wherein the width of the Vertebral Body Replacement device is less than twelve millimeters and the height of the Vertebral Body Replacement device is equal to the width.

15. A method of providing a Vertebral Body Replacement device for placement into a cervical spine between two endplates of a single vertebra during the course of an anterior spinal surgical procedure upon the cervical spine wherein the Vertebral Body Replacement device has a width of less than twelve millimeters, the width representing side-to-side dimensions of the Vertebral Body Replacement device after it has been placed into the cervical spine, wherein the Vertebral Body Replacement device has been given a PLR product code from the Food and Drug Administration (FDA).

16. The method of claim 15, further comprising:

providing a series of Vertebral Body Replacement devices; and selecting at least one Vertebral Body Replacement device from the series of Vertebral Body Replacement devices for placement into the cervical spine.

17. The method of claim 15, wherein the Vertebral Body Replacement device engages at least a portion of two adjacent vertebrae in the cervical spine.

18. The method of claim 15, wherein the Vertebral Body Replacement device includes a space for placement of bone graft therein.

* * * * *